US012678028B2

(12) United States Patent
Zhao

(10) Patent No.: US 12,678,028 B2
(45) Date of Patent: Jul. 14, 2026

(54) REVERSAL SYSTEM FOR A SURGICAL INSTRUMENT

(71) Applicant: OLYMPUS Winter & Ibe GmbH, Hamburg (DE)

(72) Inventor: Jianxin Zhao, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 185 days.

(21) Appl. No.: 18/773,249

(22) Filed: Jul. 15, 2024

(65) Prior Publication Data

US 2025/0049304 A1     Feb. 13, 2025

Related U.S. Application Data

(60) Provisional application No. 63/531,082, filed on Aug. 7, 2023.

(51) Int. Cl.
*A61B 1/00* (2006.01)
*A61B 1/313* (2006.01)
*G02B 23/24* (2006.01)

(52) U.S. Cl.
CPC ...... *A61B 1/00163* (2013.01); *G02B 23/2446* (2013.01); *A61B 1/3132* (2013.01)

(58) Field of Classification Search
CPC .... A61B 1/002; A61B 1/055; G02B 13/0095; G02B 23/2446
USPC ................................................ 359/434, 435
See application file for complete search history.

(56) References Cited

U.S. PATENT DOCUMENTS

| | | | | |
|---|---|---|---|---|
| 4,171,872 | A * | 10/1979 | Baker ..................... | G02B 13/22 |
| | | | | 359/708 |
| 4,783,154 | A * | 11/1988 | Takahashi .......... | G02B 23/2446 |
| | | | | 359/648 |
| 6,817,975 | B1 * | 11/2004 | Farr .................... | G02B 23/2446 |
| | | | | 600/162 |
| 10,859,811 | B2 | 12/2020 | Ushio | |
| 11,497,385 | B2 | 11/2022 | Zhao | |
| 2002/0036832 | A1 * | 3/2002 | Schultz ................. | G03F 7/7005 |
| | | | | 359/651 |
| 2005/0248856 | A1 * | 11/2005 | Omura ............... | G02B 17/0892 |
| | | | | 359/726 |
| 2014/0226203 | A1 * | 8/2014 | Nakano .............. | G02B 17/0856 |
| | | | | 359/728 |
| 2019/0004307 | A1 * | 1/2019 | Ushio .................... | G02B 23/26 |
| 2022/0139665 | A1 * | 5/2022 | Schubert ................ | H01J 37/28 |
| | | | | 250/307 |

* cited by examiner

*Primary Examiner* — Michael J Carey
*Assistant Examiner* — Stephen Floyd London
(74) *Attorney, Agent, or Firm* — Scully, Scott, Murphy & Presser, P.C.

(57)     ABSTRACT

A reversal system for a surgical instrument including: first and second outer achromats each having, first and second lenses, and first and second inner achromats arranged between the first and second outer achromats. Each of the first and second inner achromats having first and second lenses. A first pair of the first outer achromat and the first inner achromat being arranged symmetrically with respect to a second pair of the second outer achromat and the second inner achromat.

12 Claims, 2 Drawing Sheets

1

REVERSAL SYSTEM FOR A SURGICAL INSTRUMENT

CROSS-REFERENCE TO RELATED APPLICATION

The present application is based upon and claims the benefit of priority from U.S. Provisional Application No. 63/531,082 filed on Aug. 7, 2023, the entire contents of which is incorporated herein by reference.

BACKGROUND

Field

The present disclosure relates to a reversal system and more particularly to a reversal system for use with a surgical instrument, such as an endoscope. Moreover, the present disclosure relates to a use of a reversal system. Still further, the present disclosure relates to a surgical instrument, such as endoscope, as well as a method of operating a surgical instrument, such as an endoscope.

Prior Art

As is known in the prior art, rigid endoscopes normally have an optical system which consists of an objective, an eyepiece and a relay lens system arranged therebetween, wherein the relay lens system has several reversal systems. Normally, an uneven number of reversal systems is provided since the objective and each reversal system generates a reversed image, and a normal endoscope should generate an upright image, whereby the generated image is orientated upright. In order to correct significant imaging errors, a symmetrical design of reversal systems is provided.

For example, a reversal system for an optical system of a rigid endoscope is known from DE 11 2004 002 220 B4. Furthermore, DE 10 2012 200 146 A1 describes a reversal system for an endoscope with a plurality of equivalent reversal systems.

Moreover, it is known that lengthened endoscopes (e.g. laparoscopes) with additional shorter reversal systems as minimal invasive surgery instruments are provided or used for bariatric surgeries.

SUMMARY

It is an object to provide, optics having a small (outer) diameter and a short length for bariatric surgical instruments, such as a laparoscope or the like, with an enhanced resolution and which may be inexpensive. Another object is to provide a surgical instrument for bariatric surgeries with improved optical properties or performance.

Such object can be solved by a reversal system for a surgical instrument, such as an endoscope, with two outer achromats, which can be exclusive, each having, two lenses, which can be exclusive, and with two inner achromats, which can be exclusive, arranged between the outer achromats, each of the inner achromats having two lenses, which can be exclusive, the pairs with one outer achromat and one inner achromat each being arranged symmetrically with respect to one another, wherein the reversal system satisfies the following condition:

$$\frac{L * NA^2}{D^2 * \left(\Phi_{RMS} + \frac{|PTZ|}{10}\right)} > 5,$$

2 wherein:

L is a length of the reversal system/mm,

NA is a numerical aperture,

D is an (outer) diameter of the reversal system/mm, $\Phi_{RMS}$ is the minimum RMS (Root Mean Square) spot diameter at the center/mm, which can be polychromatic,

|PTZ| is an absolute value of a (third order) curvature of a Petzval surface, wherein PTZ is given by the formula $$PTZ = \frac{-S_4}{I^2}$$

wherein $S_4$ is a Petzval sum (third order) and I is a Helmholtz-Lagrange invariant.

An optical system is provided as a reversal system for a surgical instrument, for example, a 5.4 mm laparoscope or the like, which has a small diameter, e.g. <4 mm, and a short length, wherein the optical quality of the reversal system is enhanced in the center and especially at the edges. In addition, the reversal system also provides high resolution while maintaining high brightness and contrast. The length of the reversal system, the (outer) diameter of the reversal system and the minimum RMS (Root Mean Square) spot diameter at the center are each expressed in millimeters (mm).

With the reversal system, the mentioned formula takes into account the quality of the system at the center and at the edge as well as ratio of total length and brightness.

The outer achromats as well as the inner achromats can be configured as glued or cemented doublet achromats.

According to a further embodiment of the reversal system, the lenses of the inner achromats and the lenses of the outer achromats can have the same diameter, such as the same outer diameter.

The diameter of the lenses of the inner achromats and the diameter of the lenses of the outer achromats can be less than 4.00 mm. For example, the diameter of the lenses can be 3.75 mm.

The inner achromats can each have a negative lens (diverging lens) and a positive lens (converging lens) and/or the outer achromats can each have a negative lens (diverging lens) and a positive lens (converging lens).

Such object can also be achieved by a use of a reversal system, as described above, for a surgical instrument, such as an endoscope, for performing a surgical operation, such as a bariatric operation. The surgical instrument can be configured with at least one above-described reversal system. To avoid repetitions, explicit reference is made to the statements above.

Such object can also be solved by a surgical instrument, such as an endoscope, with at least one reversal system, wherein the endoscope can be provided with at least one reversal system, as described above.

Such object can also be solved by a method of operating a surgical instrument, such as an endoscope, for performing a surgical operation, such as a bariatric operation, wherein the surgical instrument can be provided with a reversal system, as described above. In order to avoid repetitions, reference is expressly made to the above statements.

BRIEF DESCRIPTION OF THE DRAWINGS

Further features will become evident from the description of embodiments, together with the claims and the appended drawings. Embodiments can fulfill individual features or a combination of several features.

The embodiments described below, without restricting the general intent of the invention, based on exemplary embodiments, wherein reference is made expressly to the drawings with regard to the disclosure of all details that are not explained in greater detail in the text.

In the drawings:

Figure 1:
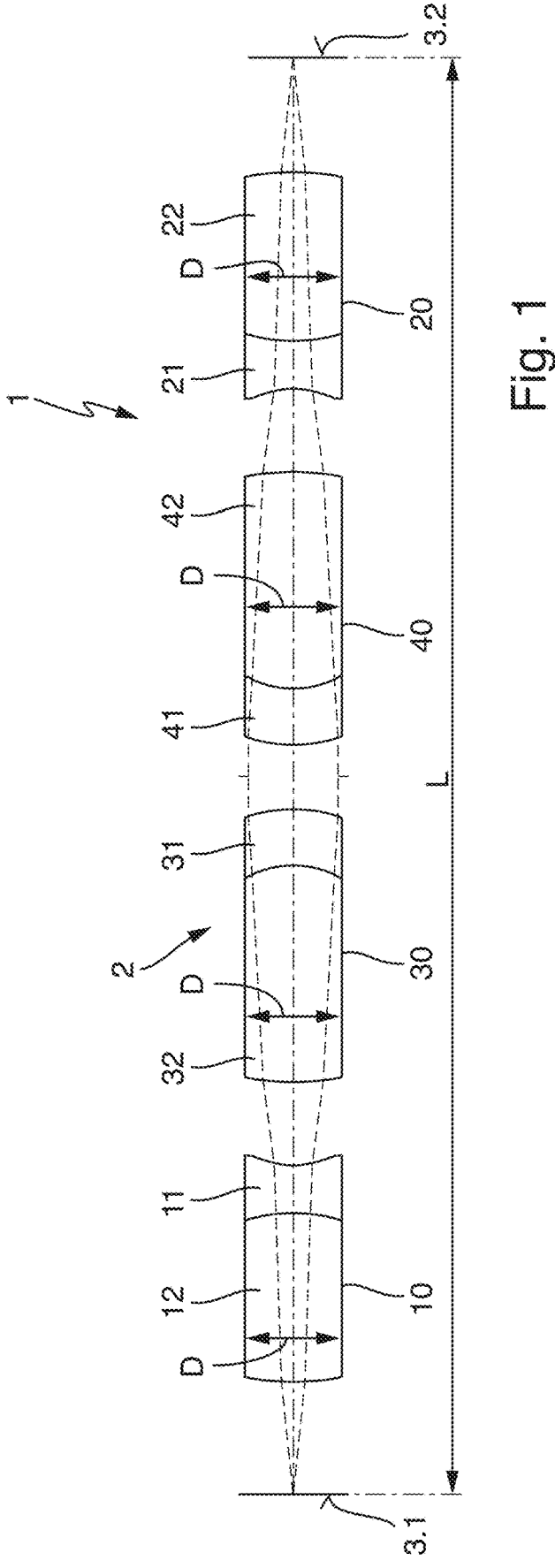
Figure 2A:
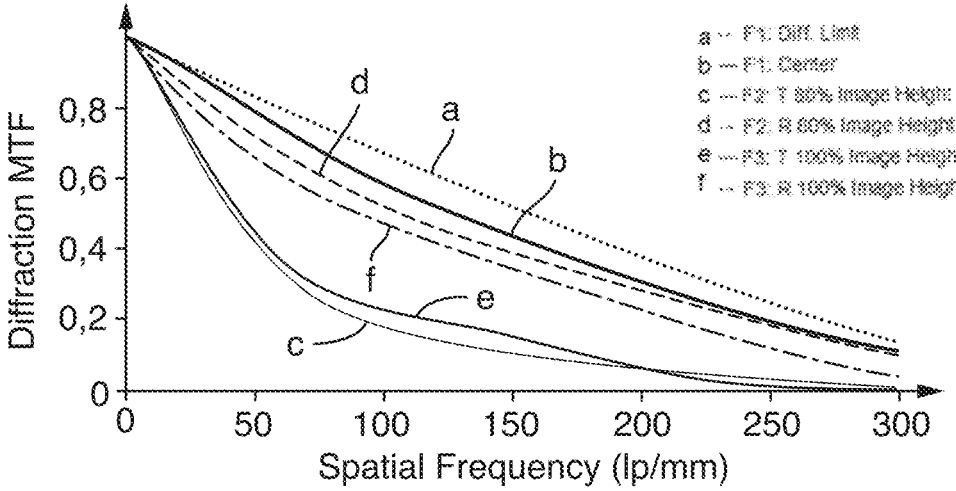
Figure 2B:
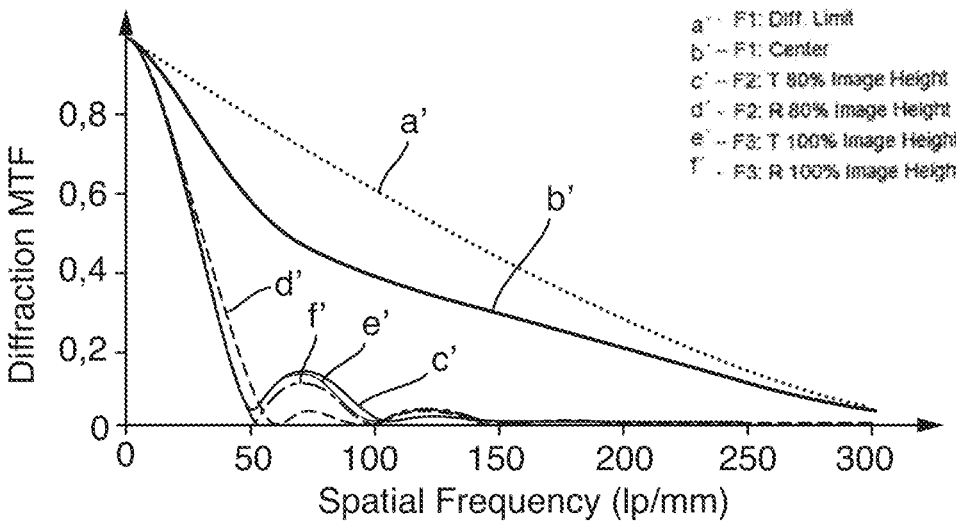

FIG. 1 schematically illustrates a portrayal of a reversal system for an endoscope, FIG. 2*a* illustrates a diffraction diagram MTF (Modulation Transfer Function) of an optical system with a reversal system, and FIG. 2*b* illustrates a diffraction diagram MTF (Modulation Transfer Function) of an optical system of a bariatric optical system (according to the prior art).

DETAILED DESCRIPTION

FIG. 1 schematically illustrates a reversal system 2 for a schematically identified surgical instrument 1. The surgical instrument 1 can be provided as a laparoscope or an endoscope. The surgical instrument 1 can be configured as a rigid surgical instrument.

The reversal system 2 in this case is a component of an optical system of the surgical instrument 1. The optical system of the surgical instrument 1 in this case can be arranged in a rigid tube (not shown). The optical system of the surgical instrument 1 may comprise an objective at the distal end, wherein the image generated by the objective is transmitted for example using a plurality of reversal systems to an image plane at the proximal end on which the image may be viewed by an eyepiece. A camera can also be arranged on the eyepiece.

The reversal system 2 shown in FIG. 1 of the optical system of the surgical instrument 1 transmits the image from a first image plane 3.1 to a second image plane 3.2. The image, which is present in the image plane 3.1, is shown in reverse on, or respectively in, the image plane 3.2. In so doing, the image of the image plane 3.1 is inverted in the image plane 3.2.

The reversal system 2 has first and second outer achromats 10, 20 between which two inner achromats 30, 40 are arranged. A first outer achromat 10 comprises a biconcave lens 11 and a biconvex lens 12. Correspondingly, a second outer achromat 20 has a biconcave lens 21 and a biconvex lens 22. The lenses 11, 12 of the first outer achromat 10 as well as the lenses 21, 22 of the second outer achromat 20 can be configured circular in cross-section, i.e., perpendicular to the plane of the drawing (perpendicular to an optical axis O), and have in this case a constant (outer) diameter D, for example 3.75 mm.

First and second inner achromats 30, 40 are arranged between the first and second outer achromats 10, 20 each have a convex-concave lens 31, 41, as well as a biconvex lens 32, or respectively 42. The lenses 31, 32 of the first inner achromat 30 as well as the lenses 41, 42 of the second inner achromat 40 can be configured circular in cross-section, and have the same diameter D as the first and second outer achromats 10, 20. The reversal system 2 with the first and second outer achromats 10, 30 and the first and second inner achromats 20, 40 has a length L, which is the distance between the image planes 3.1 and 3.2.

The first and second inner achromats 30, 40, or respectively, the lenses 31, 32, 41, 42 of the first and second inner achromats 30, 40 can be arranged in a sleeve or in a shaft (or the like) and accommodated therein.

The first and second outer achromats 10, 30 and the first and second inner achromats 20, 40 are arranged symmetrically to each other. Thus, the pair with the first outer achromat 10 and the first inner achromat 30 is arranged symmetrically with the other pair with the first outer achromat 20 and the first inner achromat 40.

The reversal system can satisfy the following condition $$\frac{L * NA^2}{D^2 * \left(\Phi_{RMS} + \frac{|PTZ|}{10}\right)} > 5,$$

wherein

L is the length of the reversal system 2/mm,

NA is the numerical aperture of the reversal system 2,

D is the (outer) diameter of the reversal system 2/mm, $\Phi_{RMS}$ is the minimum, in particular polychromatic, RMS (Root Mean Square) spot diameter at the center/mm,

|PTZ| is the absolute value of the (third order) curvature of the Petzval surface, wherein PTZ is given by the formula $$PTZ = \frac{-S_4}{I^2},$$

wherein $S_4$ is the Petzval sum (third order) and I is the Helmholtz-Lagrange invariant. The length of the reversal system, the (outer) diameter of the reversal system and the minimum RMS (Root Mean Square) spot diameter at the center are each specified in millimeters (mm).

FIGS. 2*a* and 2*b* show the modulation transfer functions (MTF) of an optical system with the reversal system 2 according to the present disclosure (see FIG. 2*a*) and a bariatric optical system (according to the prior art) (see FIG. 2*b*). The horizontal axis shows the spatial frequency (lp/mm), and the vertical axis shows the MTF, also contrast.

The MTF describes the optical system in terms of contrast at different spatial frequencies, expressed in line pairs per mm (lp/mm). Higher spatial frequencies correspond to finer details. An MTF value of 1 means perfect contrast, 0 is no contrast at all, white and black lines cannot be distinguished anymore at all.

Generally, the solid lines represent MTF in the tangential direction and the dashed lines represent MTF in the sagittal direction. MTF a/a' represented by dotted lines represent the theoretical ideal case of a diffraction-limited system of each optics. As can be seen in FIG. 2*b*, even the theoretical optimum involves the MTF decreasing rapidly towards finer details.

Lines b and b' denote the MTF in the center of the image plane, which is the same in the sagittal and tangential directions. Lines c, c' and d, d' denote the MTF at 80% image height in the tangential and sagittal directions, respectively, lines e, e' and f, f' the MTF at 100% image size, i.e., at the far edge.

As can be seen in FIG. 2*b*, the MTF of the bariatric optical system has worse MTF values, especially the contrast (MTF) at the edge areas become catastrophic.

In the case of an optical system with the reversal system 2 according to the present disclosure, shown in FIG. 2*a*, the values are significantly better, not only on the center area, also on the edge area. The MTFs are overall significantly improved, especially at high spatial frequencies, leading to clearer and more detailed images.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

1 Surgical instrument
2 Reversal system
3.1, 3.2 Image plane
10 Achromat
11 Biconcave lens
12 Biconvex lens
20 Achromat
21 Biconcave lens
22 Biconvex lens
30 Inner achromat
31 Convex-concave lens
32 Biconvex lens
40 Inner achromat
41 Convex-concave lens
42 Biconvex lens
D Diameter
L Length
O Optical Axis

The invention claimed is:

1. A reversal system for a surgical instrument comprising:
first and second outer achromats each having, first and second lenses, and
first and second inner achromats arranged between the first and second outer achromats, each of the first and second inner achromats having first and second lenses, a first pair of the first outer achromat and the first inner achromat being arranged symmetrically with respect to a second pair of the second outer achromat and the second inner achromat, wherein the reversal system satisfies the following condition $$\frac{L * NA^2}{D^2 * \left( \Phi_{RMS} + \frac{|PTZ|}{10} \right)} > 5,$$

wherein
L is a length of the reversal system/mm,
NA is a numerical aperture,
D is an outer diameter of the reversal system/mm,
$\Phi_{RMS}$ is the minimum RMS (Root Mean Square) spot diameter at a center/mm,
|PTZ| is an absolute value of a (third order) curvature of a Petzval surface, wherein PTZ is given by the formula $$PTZ = \frac{-S_4}{I^2},$$

wherein $S_4$ is a Petzval sum (third order) and I is a Helmholtz-Lagrange invariant.

2. The reversal system according to claim 1, wherein the minimum RMS spot diameter is a polychromatic RMS spot diameter.

3. The reversal system according to claim 1, wherein the first and second outer achromats are exclusive.

4. The reversal system according to claim 1, wherein the first and second lenses of the first and second outer achromats are exclusive.

5. The reversal system according to claim 1, wherein the first and second inner achromats are exclusive.

6. The reversal system according to claim 1, wherein the first and second lenses of the first and inner outer achromats are exclusive.

7. The reversal system according to claim 1, wherein the first and second lenses of each of the first and second inner achromats and the first and second lenses of each the first and second outer achromats have a same diameter.

8. The reversal system according to claim 1, wherein a diameter of the first and second lenses of each of the first and second inner achromats and a diameter of the first and second lenses of each of the first and second outer achromats is less than 4.00 mm.

9. The reversal system according to claim 1, wherein one or more of:
the first and second lenses of each of the first and second inner achromats comprise a negative lens (diverging lens) and a positive lens (converging lens); and
the first and second lenses of each of the first and second outer achromats comprise a negative lens (diverging lens) and a positive lens (converging lens).

10. A surgical instrument comprising:
at least one reversal system according to claim 1.

11. An endoscope comprising:
at least one reversal system according to claim 1.

12. A method of operating a surgical instrument for performing a surgical operation, the method comprising:
providing the surgical instrument with at least one reversal system according to claim 1.

* * * * *